United States Patent
Yu et al.

(10) Patent No.: US 12,234,208 B2
(45) Date of Patent: Feb. 25, 2025

(54) 3,4-DIHYDROXY-N-(1'-BENZYL-2'-HYDROXYETHYL)-2-METHYLPYRIDINE CHLORIDE, AND SYNTHESIS AND USE THEREOF

(71) Applicant: HANGZHOU ZEDE PHARMA-TECH CO. LTD., Zhejiang (CN)

(72) Inventors: Yongping Yu, Hangzhou (CN); Robert Charles Hider, London (GB); Xin Yuan, Hangzhou (CN); Feng Han, Nanjing (CN); Wenteng Chen, Hangzhou (CN); Guolin Zhang, Hangzhou (CN); Zudong Liu, Hangzhou (CN); Yu Zhang, Nanjing (CN)

(73) Assignee: HANGZHOU ZEDE PHARMA-TECH CO. LTD., Hangzhou (CN)

( * ) Notice: Subject to any disclaimer, the term of this patent is extended or adjusted under 35 U.S.C. 154(b) by 508 days.

(21) Appl. No.: 17/849,677

(22) Filed: Jun. 26, 2022

(65) Prior Publication Data

US 2022/0356156 A1    Nov. 10, 2022

Related U.S. Application Data

(63) Continuation of application No. PCT/CN2020/097578, filed on Jun. 23, 2020.

(30) Foreign Application Priority Data

Jan. 19, 2020   (CN) .......................... 202010063101.9

(51) Int. Cl.
  *C07D 213/69*    (2006.01)
  *A61P 25/16*    (2006.01)

(52) U.S. Cl.
  CPC ............ *C07D 213/69* (2013.01); *A61P 25/16* (2018.01)

(58) Field of Classification Search
  CPC ............................... C07D 213/69; A61P 26/16
  See application file for complete search history.

(56) References Cited

U.S. PATENT DOCUMENTS

2006/0234927 A1* 10/2006 Youdim .................. A61P 43/00
                                                       514/6.9

FOREIGN PATENT DOCUMENTS

| CN | 101679263 A | 3/2010 |
| CN | 102869256 A | 1/2013 |
| CN | 111170936 A | 5/2020 |
| EP | 1006108 A1 | 6/2000 |
| EP | 1027335 A1 | 8/2000 |
| EP | 1565185 A2 | 8/2005 |

(Continued)

OTHER PUBLICATIONS

Notice of Allowance(JP2022538312); Date of Mailing: Jul. 3, 2023.
Effectiveness-of-the-Iron-Chelator-CN128-in-Mitigating-the-Formation-of-Dopamine-Oxidation-Products-Associated-with-the-Progression-of-Parkinson's-Disease.
International Search Report (PCT/CN2020/097578); Date of Mailing: Oct. 12, 2020.
CN First Office Action(202010063101.9); Date of Mailing: Oct. 10, 2020.

*Primary Examiner* — Timothy R Rozof
(74) *Attorney, Agent, or Firm* — W&G Law Group

(57) ABSTRACT

The present application provides the preparation and use of a 3,4-dihydroxyl-N-(1'-benzyl-2'-hydroxyethyl)-2-methyl pyridine chloride. According to the present application, a 3,4-dihydroxyl-N-(1'-benzyl-2'-hydroxyethyl)-2-methyl pyridine chloride is directly synthesized by a one-step reaction, and the compound includes a pharmaceutically acceptable salt thereof. 3,4-dihydroxyl-N-(1'-benzyl-2'-hydroxyethyl)-2-methyl pyridine chloride has been proved to have a good antiparkinsonian activity by animal tests, and it is a class of novel antiparkinsonian drug candidates. It can be used in the preparation of drugs for the treatment of a Parkinson's disease, and its structural formula (I) is as follows:

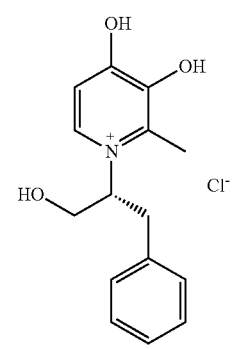

A

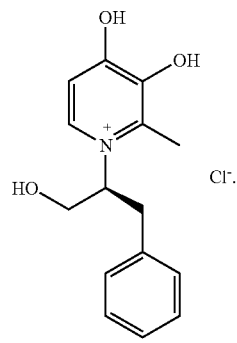

B

6 Claims, 2 Drawing Sheets

(56) References Cited

FOREIGN PATENT DOCUMENTS

| WO | 9923075 | A1 | 5/1999 |
| WO | 200322817 | A1 | 3/2003 |
| WO | 2004041151 | A2 | 5/2004 |
| WO | 2009103950 | A1 | 8/2009 |

* cited by examiner

3,4-DIHYDROXY-N-(1'-BENZYL-2'-HYDROXYETHYL)-2-METHYLPYRIDINE CHLORIDE, AND SYNTHESIS AND USE THEREOF

TECHNICAL FIELD

The present application relates to the field of organic synthesis and pharmaceutical chemistry, specifically relating to a 3,4-dihydroxyl-N-(1'-benzyl-2'-hydroxyethyl)-2-methyl pyridine chloride and use thereof in the preparation of drugs for the treatment of the Parkinson's disease.

BACKGROUND

Parkinson's disease (PD), also known as tremor paralysis, is a common degenerative disease of the central nervous system, mainly clinically characterized by static tremor, muscular rigidity, motor retardation and postural reflex disorders. The exact etiology and pathogenesis of PD are not fully understood, and the major pathological changes are noted by the degenerative death of neurons secreted by dopamine (DA) and the formation of Lewy Body within the substantia nigra. Among them, a variety of factors may be involved in the degenerative death process of PD dopaminergic neurons, such as genetic factors, environmental factors, aging, oxidative stress, mitochondrial functional defects, etc. Currently, the prevalence rate of Parkinson's disease among people over the age of 65 in China is about 1.7%, and the number of patients increases with the aging of the population. PD not only has a high prevalence rate, but is also a lifelong disease. With the development of the diseased period, the patient gradually loses the ability to live and work, and suffers from non-motor complications such as cognitive impairment and mental disorder, which seriously affects the quality of life. The patient needs long-term medication, which brings a heavy burden to the family and society.

At present, the therapeutic drugs for PD are mainly dopamine-replacing drugs and dopaminergi-affecting drugs. Although long-term treatment may lead to serious adverse reactions, such as hyperactivity disorder, dyspraxia and movement fluctuation, and efficacy decline in patients with advanced stage, levodopa (Madopar®) is still the most effective symptomatic treatment drug for PD at present. Another class of dopaminergic drug is dopamine receptor agonist, which also plays an important role in PD therapy. By simulating endogenous neurotransmitters, they directly act on dopamine receptors to activate them and play a dopamine-like role, such as Rotigotine, Pramipexol and Ropinirole. However, this dopamine replacement strategy is mainly for symptomatic treatment, it cannot effectively prevent or alleviate the progression of PD disease, and eventually leads to severe movement disorder and dementia.

Therefore, the discovery of novel anti-PD drugs is of great significance.

SUMMARY

The present application is directed to provide a 3,4-dihydroxyl-N-(1'-benzyl-2'-hydroxyethyl)-2-methyl pyridine chloride having the following structure formula of Formula (I), wherein a compound A in the Formula (I) has a R configuration and a compound B in the Formula (I) has a S configuration.

(I)

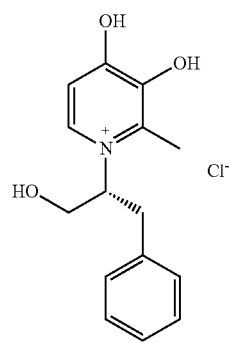

A

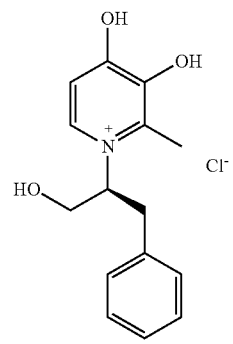

B

The compounds of Formula (I) include pharmaceutically acceptable salts thereof, and solvates of the compounds of Formula (I) or the pharmaceutically acceptable salts thereof, tautomer, or a mixture thereof in any proportion, including a racemic mixture.

On the other hand, the present application is directed to provide a method for preparing 3,4-dihydroxyl-N-(1'-benzyl-2'-hydroxyethyl)-2-methyl pyridine chloride, including the following steps:

(1) successively adding methyl maltol, phenylalaninol, a boron reagent and water into a three-necked flask and stirring for 2-10 hours at a certain temperature until the reaction was complete, wherein a molar ratio of the methyl maltol to the phenylalaninol is 1:1-1:1.2 (preferably 1:1.1) and a molar ratio of the methyl maltol to the boron reagent is 1:0.8-1:1.2 (preferably 1:1); wherein 5 ml of water is used for every 1 g of methylmaltol, and the reaction is carried out under stirring at the temperature range from 60° C. to 100° C. for 2-10 hours until the reaction complete; the boron reagent is selected from boric acid, phenylboric acid and sodium borate;

(2) adjusting a pH value of a reaction system obtained from step (1) to 8.5 with a 0.01 mol/mL sodium hydroxide solution, and extracting the reaction system with dichloromethane; combining organic phases, and then adding a 6 mol/L hydrochloric acid solution; refluxing for 1 hour, and subsequently crystallizing at −5° C. to 5° C. for 12 hours; carrying out suction filtration and washing with dichloromethane, wherein the washing method is that 1 g filter cake is washed with dichloromethane twice, and the dosage of dichloromethane is 3 ml each time, so as to obtain a white solid product.

The reaction equation is as follows:

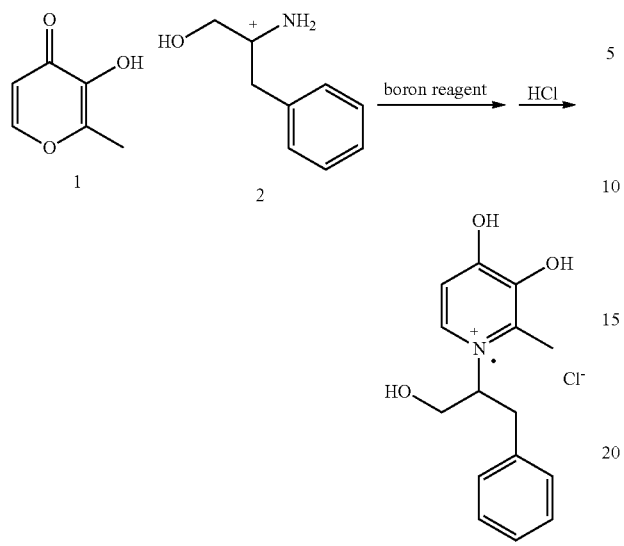

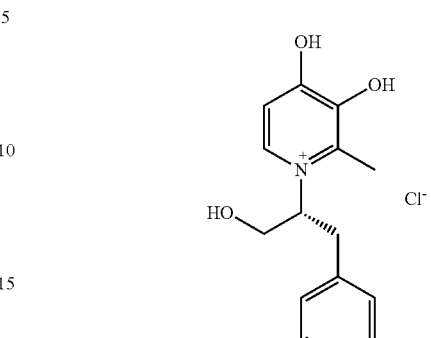

Another purpose of the present application is to provide use of 3,4-dihydroxyl-N-(1'-benzyl-2'-hydroxyethyl)-2-methyl pyridine chloride in the preparation of antiparkinsonian drug. The compound has been proved to have a good antiparkinsonian activity in animal model.

The present application has the following advantages over the existing technologies: (1) direct synthesis of a 3,4-dihydroxyl-N-(1'-benzyl-2'-hydroxyethyl)-2-methyl pyridine chloride in one-pot reaction; (2) 3,4-dihydroxyl-N-(1'-benzyl-2'-hydroxyethyl)-2-methyl pyridine chloride provided by the present application has been proved to have a good antiparkinsonian activity in animal model, and is a novel class of antiparkinsonian drug candidates.

DESCRIPTION OF EMBODIMENTS

Figure 1:
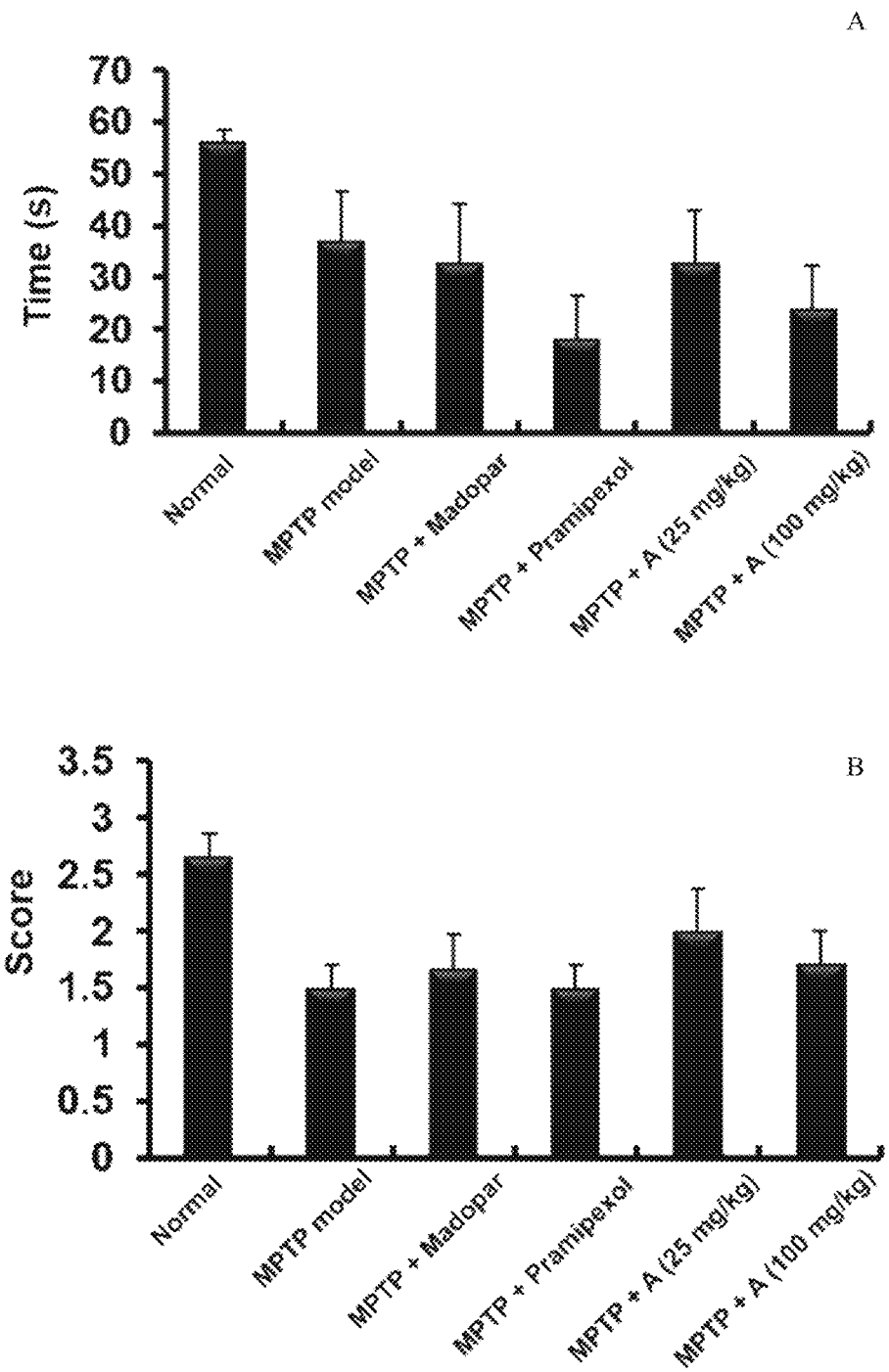
FIG. 1 shows the result of a compound A in a chronic MPTP mouse model in a motor function test, where A. traction test (time); B. traction test (score).

The present application will be further illustrated below with reference to the specific embodiments and figures.

Example 1 Preparation of a (R)-3,4-dihydroxyl-N-(1'-benzyl-2'-hydroxyethyl)-2-methyl pyridine chloride (compound A)

Methyl maltol (16 mmol, 2.02 g), D-phenylalaninol (17.6 mmol, 2.66 g), boric acid (16 mmol, 1.95 g) and 10 mL water were successively added to a 50 mL three-necked flask, and the reaction was completed after 2 hours at 100° C. The reaction solution was adjusted to a pH of about 8.5 with a sodium hydroxide solution (0.01 mol/mL), extracted with dichloromethane (10 mL×3); a 20 mL hydrochloric acid solution (6 mol/L) was added after the combination of the organic phases, the solution was stirred at reflux for 1 hour, and then stirred for crystallization at −5° C. to 5° C. for 12 hours; washing was carried out with dichloromethane (10 mL×2), 3.42 g white solid was obtained with a yield of 72%.

The structural formula of the compound A is as follows:

Melting point: 177-179° C., $^1$H NMR (500 MHz, DMSO-$d_6$) δ 10.37 (s, 1H), 8.58 (d, J=7.5 Hz, 1H), 7.43 (d, J=7.0 Hz, 1H), 7.24 (t, J=7.2 Hz, 2H), 7.19-7.16 (m, 3H), 5.36 (s, 1H), 5.10-5.04 (m, 1H), 3.90-3.82 (m, 2H), 3.27 (dd, J=14.0, 5.5 Hz, 1H), 3.12 (dd, J=14.0, 10.0 Hz, 1H), 2.30 (s, 3H). $^{13}$C NMR (125 MHz, DMSO-$d_6$) δ 158.5, 142.5, 142.1, 136.2, 135.3, 128.9, 128.6, 126.9, 110.8, 66.7, 63.0, 36.2, 12.6. HRMS (ESI): m/z calcd for $C_{15}H_{18}NO_3^+$[M+H]$^+$: 260.1287, found: 260.1289.

The following are controlled experiments with different conditions.

Comparative Example 1-1, the reaction temperature was changed from 100° C. to 60° C., and the rest were the same as Example 1. 2.47 g of a white solid (R)-3,4-dihydroxyl-N-(1'-benzyl-2'-hydroxyethyl)-2-methyl pyridine chloride was obtained, with a yield of 52%.

Comparative Example 1-2, the amount of D-phenylalaninol was changed to (16 mmol, 2.42 g), that is, methyl maltol: D-phenylalaninol (molar ratio)=1:1, and the rest were the same as Example 1. 2.66 g of a white solid (R)-3,4-dihydroxyl-N-(1'-benzyl-2'-hydroxyethyl)-2-methyl pyridine chloride was obtained, with a yield of 56%.

Comparative Example 1-3, the amount of D-phenylalaninol was changed to (19.2 mmol, 2.90 g), that is, methyl maltol: D-phenylalaninol (molar ratio)=1:1.2, and the rest were the same as Example 1. 3.51 g of a white solid (R)-3,4-dihydroxyl-N-(1'-benzyl-2'-hydroxyethyl)-2-methyl pyridine chloride was obtained, with a yield of 74%.

Comparative Example 1-4, the amount of boric acid was changed to (12.8 mmol, 1.94 g), that is, methyl maltol: boric acid (molar ratio)=1:0.8, and the rest were the same as Example 1. 3.04 g of a white solid (R)-3,4-dihydroxyl-N-(1'-benzyl-2'-hydroxyethyl)-2-methyl pyridine chloride was obtained, with a yield of 64%.

Comparative Example 1-5, the amount of boric acid was changed to (19.2 mmol, 2.34 g), that is, methyl maltol: boric acid (molar ratio)=1:1.2, and the rest were the same as Example 1. 3.51 g of a white solid (R)-3,4-dihydroxyl-N-(1'-benzyl-2'-hydroxyethyl)-2-methyl pyridine chloride was obtained, with a yield of 74%.

Comparative Example 1-6, boric acid was changed to phenylboric acid, and the rest were the same as Example 1. 2.85 g of a white solid (R)-3,4-dihydroxyl-N-(1'-benzyl-2'-hydroxyethyl)-2-methyl pyridine chloride was obtained, with a yield of 60%.

Comparative Example 1-7, boric acid was changed to sodium borate, and the rest were the same as Example 1.

2.47 g of a white solid (R)-3,4-dihydroxyl-N-(1'-benzyl-2'-hydroxyethyl)-2-methyl pyridine chloride was obtained, with a yield of 52%.

Example 2 Preparation of a (S)-3,4-dihydroxyl-N-(1'-benzyl-2'-hydroxyethyl)-2-methyl pyridine chloride (compound B)

Methyl maltol (16 mmol, 2.02 g), L-phenylalaninol (17.6 mmol, 2.66 g), boric acid (16 mmol, 1.95 g) and 10 ml water were successively added to a 50 mL three-necked flask, and the reaction was completed after 2 hours at 100° C. The reaction solution was adjusted to a pH of about 8.5 with a sodium hydroxide solution (0.01 mol/mL), extracted with dichloromethane (10 mL×3); a 20 mL hydrochloric acid solution (6 mol/L) was added after the combination of the organic phases, the solution was stirred at reflux for 1 hour, and then stirred for crystallization at −5° C. to 5° C. for 12 hours; washing was carried out with dichloromethane (10 mL×2), 3.51 g white solid was obtained with a yield of 74%.

The structural formula of the compound B is as follows:

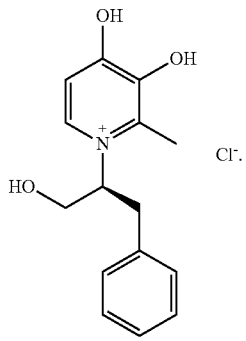

Melting point: 177-179° C., $^1$H NMR (500 MHz, DMSO-$d_6$) δ 10.38 (s, 1H), 8.59 (d, J=7.5 Hz, 1H), 7.44 (d, J=7.0 Hz, 1H), 7.25 (t, J=7.2 Hz, 2H), 7.20-7.16 (m, 3H), 5.37 (s,1H), 5.11-5.04 (m, 1H), 3.91-3.82 (m, 2H), 3.28 (dd, J=14.0, 5.0 Hz, 1H), 3.13 (dd, J=14.0, 10.5 Hz, 1H), 2.30 (s, 3H). HRMS (ESI): m/z calcd for $C_{15}H_{18}NO_3^+$[M+H]$^+$: 260.1287, found: 260.1285.

Example 3 Use of a (R)-3,4-dihydroxyl-N-(1'-benzyl-2'-hydroxyethyl)-2-methyl pyridine chloride (compound A) in Parkinson's disease Effects of the compound A in a behavioral research in a chronic 1MPTP mouse model:

1. Preparation of the Chronic MPTP Mouse Model

A chronic MPTP (1-methyl-4-phenyl-1,2,3,6-tetrahydropyridine) mouse model was prepared to simulate PD. 250 mg/kg probenecid was intraperitoneally injected into the mice and then 25 mg/kg MPTP was intraperitoneally injected 0.5 hour later. Injection was implemented every 3.5 days for 5 weeks. MPTP was converted into metabolite MPP$^+$ by monoamine oxidase B in glial cells after crossing the blood-brain barrier. Due to its high affinity for dopamine transporters, MPP$^+$ can easily enter dopaminergic neurons. By inhibiting the toxic effect of the mitochondrial complex I, it can cause oxidative stress and break intracellular calcium homeostasis, thus causing the apoptosis or necrosis of dopaminergic neurons, and finally achieving the goal of simulating PD. Probenecid was used to prevent the rapid clearance and excretion of MPTP in the brain and kidneys. In the process of model preparation, the amount of probenecid had no significant influence on the content of the dopamine in the brain.

2. Grouping of Experimental Animals and Dosage of Drug Administration

Thirty-six C57/BL mice were divided into six groups (n≥6), as shown in Table 1.

TABLE 1

| No. | Groups | Dosage of drug administration |
|---|---|---|
| 1 | C57 Normal control | Saline |
| 2 | Chronic MPTP model | Saline |
| 3 | Chronic MPTP model + Madopar | Madopar 50 mg/kg/d |
| 4 | Chronic MPTP model + Pramipexol | Pramipexol 0.075 mg/kg/d |
| 5 | Chronic MPTP model + Compound A (25 mg/kg) | Compound A 25 mg/kg/d |
| 6 | Chronic MPTP model + Compound A (100 mg/kg) | Compound A 100 mg/kg/d |

After modeling, the mice were administrated (p.o.) with the drug for one month.

3. Method of a Behavioral Research

At the end of administration, the behavioral research was performed on the animals as following:

(1) Traction Test:

The two forepaws of the mice were suspended on a horizontal metal wire (5 mm in diameter and 30 cm from the ground), and the time for mice to fall from the metal wire was recorded, wherein a time over 60 seconds was counted as 60 seconds. The mice were trained twice a day before the test.

Evaluation Criteria for Suspension Ability of Mice:

In the first 10 seconds, the mice that grasped the wire with two hind paws were scored for 3 points, the mice that grasped the wire with one hind paw were scored for 2 points, and the mice that failed to grasp the wire were scored for 1 point. Finally, the scores were calculated and the time for the mice to fall from the metal wire were recorded, wherein a time over 60 seconds was counted as 60 seconds.

(2) Water Maze Test:

The Morris water maze test can measure the changes in cognitive and memory ability. The diameter of a circular pool was 120 cm, and the height was 70 cm. The diameter of a circular platform was 10 cm, and the height was 50 cm. The platform was 1 cm lower than the water surface, and the water temperature was (22±2)° C. A camera with a display system was placed above the water maze, and the computer automatically tracked the timing and recorded the swimming track. The external reference of the maze remained unchanged during the experiment. Orientation navigation test: the mice were trained at four entry points every day. The videos of the swimming path were recorded by the camera and computer, and the time of finding the platform from the entry point, namely the latency of escaping to the platform, was recorded. The mice were allowed to climb onto the platform and stay there for 10 seconds. If they could not find and climb onto the platform in 90 seconds, the mice were artificially guided to find the platform and stay on the platform for 10 seconds, and the latency was recorded as 90 seconds. The swimming time was limited to 90 seconds each time, and the rest interval was 30-50 minutes. The total training time was 4 days. The latency was calculated on the average of four training sessions per day. Spatial probe test: the circular platform was removed on the fifth day at the end of the orientation navigation test. The mice were launched at any entry point, the swimming track and time were recorded, and the time and times of swimming across the original platform quadrant for the first time within 90 seconds were recorded.

4. Results of the Behavioral Research (1) Traction Test:

The suspension time in the chronic MPTP model control group was significantly decreased compared with the C57 normal control group.

There was no significant difference in suspension time between the Chronic MPTP model+Madopar (50 mg/kg/d), Chronic MPTP model+Compound A (25 mg/kg) group and Chronic MPTP model+Compound A (100 mg/kg) group compared with the chronic MPTP model control group. The suspension time in the Chronic MPTP model+ Pramipexol group was decreased compared with the chronic MPTP model.

Compared with the chronic MPTP model control group, the suspension score increased in the Chronic MPTP model+ Compound A (25 mg/kg) group (FIG. 1). The results indicated that the administration of the compound A (25 mg/kg) could improve the muscle strength of PD model animals. In FIG. 1, for the C57 group, MPTP+ Compound A (25 mg/kg) group and MPTP+ Compound A (100 mg/kg) group: n=7; for the MPTP-M group, MPTP+ Madopar group, MPTP+ Pramipexol group: n=6; *p<0.05: there was a statistical difference compared with the normal control group; # p<0.05: there was a statistical difference compared with the MPTP model control group.

Figure 2:
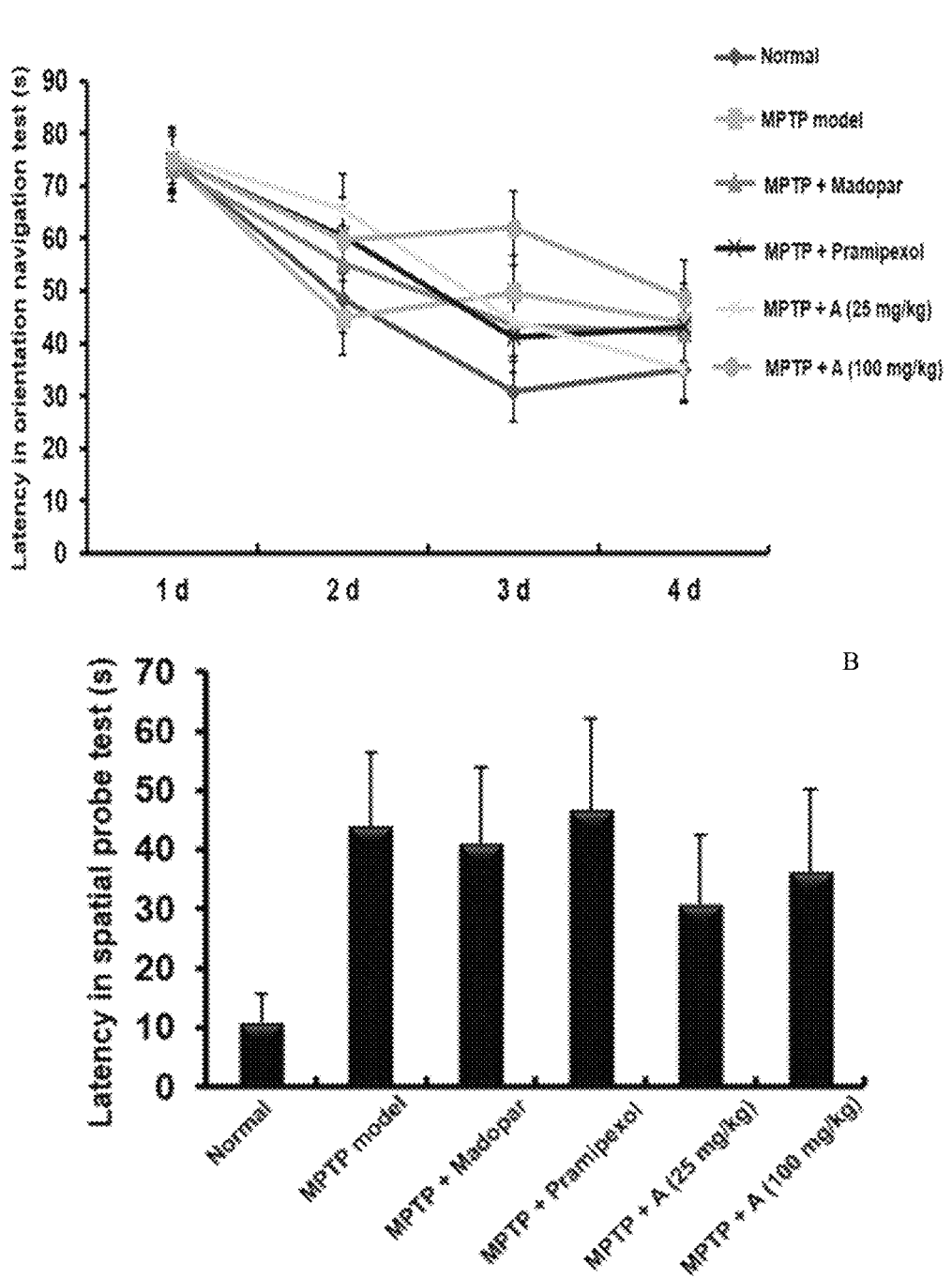
FIG. 2 shows the influence of a compound A in a chronic MPTP mouse model in a water maze test, where A. Latency in an orientation navigation test; B. Latency in a spatial probe test.

(2) Water Maze Test:

The results of the compound A in the chronic MPTP model Y maze test and the water maze test indicated that the compound A in a dosage of 100 mg/kg may improve the cognitive function of PD model animals (FIG. 2). In FIG. 2, for the C57 group, MPTP+ Compound A (25 mg/kg) group and MPTP+ Compound A (100 mg/kg) group: n=7; for the MPTP-M group, MPTP+ Madopar group, MPTP+ Pramipexol group: n=6; *p<0.05: there was a statistical difference compared with the C57 normal control group.

5. Conclusion

The compound A showed a tendency to improve muscle strength and coordination in a chronic MPTP mouse model. The compound A in a dosage of 100 mg/kg can partially improve the cognitive function in a chronic MPTP mouse model. 3,4-dihydroxyl-N-(1'-benzyl-2'-hydroxyethyl)-2-methyl pyridine chloride has a better antiparkinsonian activity.

What is claimed is:

1. A 3,4-dihydroxyl-N-(1'-benzyl-2'-hydroxyethyl)-2-methyl pyridine chloride with a structural formula as shown in Formula (I), wherein a compound A in the Formula (I) has a R configuration and a compound B in the Formula (I) has a S configuration:

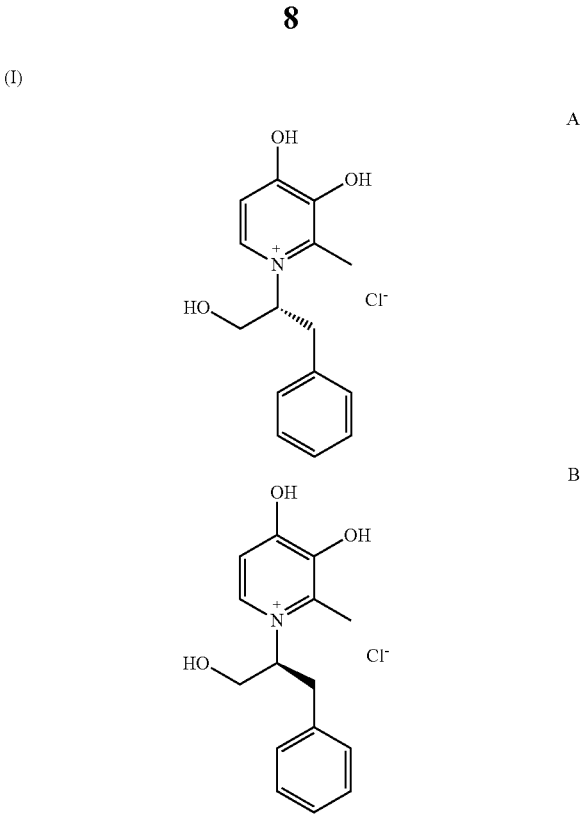

or pharmaceutically acceptable salts thereof.

2. A method for preparing 3,4-dihydroxyl-N-(1'-benzyl-2'-hydroxyethyl)-2-methyl pyridine chloride according to claim 1, comprising the following of:
 (1) successively adding methyl maltol, phenylalaninol, a boron reagent and water into a three-necked flask and stirring for 2-10 hours at a certain temperature until the reaction was complete, wherein a molar ratio of the methyl maltol to the phenylalaninol is 1:1-1:1.2, and a molar ratio of the methyl maltol to the boron reagent is 1:0.8-1:1.2; and
 (2) adjusting a pH value of a reaction system obtained from step (1) to 8.5 with a 0.01 mol/mL sodium hydroxide solution, and extracting the reaction system with dichloromethane; combining organic phases, and adding a 6 mol/L hydrochloric acid solution; refluxing for 1 hour, and crystallizing at −5° C. to 5° C. for 12 hours; carrying out suction filtration and washing a filter cake with dichloromethane to obtain a white solid.

3. The method according to claim 2, wherein the boron reagent in step (1) is selected from a group consisting of boric acid, benzene boric acid and sodium borate.

4. The method according to claim 2, wherein a range of the temperature in step (1) is 60° C. to 100° C.

5. The method according to claim 2, wherein a method of washing with dichloromethane in step (2) is as follows: washing 1 g of the filter cake twice with dichloromethane, wherein an amount of dichloromethane used each time is 3 ml.

6. A method of treating Parkinson's disease comprising administering 3,4-dihydroxyl-N-(1'-benzyl-2'-hydroxyethyl)-2-methyl pyridine chloride according to claim 1.

* * * * *